(12) United States Patent
Cernik (10) Patent No.: US 7,564,947 B2
(45) Date of Patent: Jul. 21, 2009

(54) TOMOGRAPHIC ENERGY DISPERSIVE X-RAY DIFFRACTION APPARATUS COMPRISING AN ARRAY OF DETECTORS OF ASSOCIATED COLLIMATORS

(75) Inventor: Robert Cernik, Warrington (GB)

(73) Assignee: Council for the Central Laboratory of the Research Councils (GB)

( * ) Notice: Subject to any disclaimer, the term of this patent is extended or adjusted under 35 U.S.C. 154(b) by 110 days.

(21) Appl. No.: 10/558,699

(22) PCT Filed: Dec. 4, 2003

(86) PCT No.: PCT/GB03/05281

§ 371 (c)(1),
(2), (4) Date: Nov. 30, 2005

(87) PCT Pub. No.: WO2004/106906

PCT Pub. Date: Dec. 9, 2004

(65) Prior Publication Data

US 2006/0251215 A1    Nov. 9, 2006

(30) Foreign Application Priority Data

May 31, 2003    (GB)    ................... 0312499.7

(51) Int. Cl.
*G01N 23/20*    (2006.01)
(52) U.S. Cl. .......................................... 378/71; 378/70
(58) Field of Classification Search .................. 378/57,
378/70, 71, 73, 79, 86, 87, 88, 89, 90, 147,
378/149, 154
See application file for complete search history.

(56) References Cited

U.S. PATENT DOCUMENTS

| 3,833,810 | A | * | 9/1974 | Efanov et al. ................ 378/74 |
| 3,988,585 | A | | 10/1976 | O'Neill et al. |
| 4,088,888 | A | * | 5/1978 | Brook et al. ................ 378/17 |
| 4,288,697 | A | | 9/1981 | Albert |

(Continued)

FOREIGN PATENT DOCUMENTS

DE    30 07 456 A1    9/1981

(Continued)

OTHER PUBLICATIONS

Search Report with Cover Letter, dated Sep. 12, 2003, for UK Application No. GB 0312499.7, 3 pages.

(Continued)

*Primary Examiner*—Allen C. Ho
(74) *Attorney, Agent, or Firm*—Sterne, Kessler, Goldstein & Fox P.L.L.C.

(57) ABSTRACT

A tomographic energy dispersive diffraction imaging apparatus comprises a radiation source for directing incident radiation (1, 3) at a sample (4) mounted on a support, and detection means (9, 10) mounted for detecting radiation transmitted through the sample (4) at a given angle to the direction of incidence of the radiation. The detection means comprises an array of energy dispersive detectors (9) and an array of collimators (10), such that each energy dispersive detector (9) has a respective collimator (10) associated therewith. Each collimator of the collimator array may comprise a plurality of collimator plates with apertures formed therein which are spaced apart along a direction of the transmitted radiation.

6 Claims, 7 Drawing Sheets

U.S. PATENT DOCUMENTS

| | | | |
|---|---|---|---|
| 4,951,305 A | | 8/1990 | Moore et al. |
| 5,231,655 A | | 7/1993 | Wei et al. |
| 5,263,075 A | | 11/1993 | McGann et al. |
| 5,265,144 A | * | 11/1993 | Harding et al. ............... 378/86 |
| 5,491,738 A | * | 2/1996 | Blake et al. ................... 378/71 |
| 5,589,690 A | * | 12/1996 | Siewert et al. ......... 250/390.06 |
| 5,629,524 A | * | 5/1997 | Stettner et al. ......... 250/370.09 |
| 5,787,145 A | * | 7/1998 | Geus ........................... 378/71 |
| 5,802,138 A | * | 9/1998 | Glasser et al. ............. 378/98.8 |
| 5,835,561 A | | 11/1998 | Moorman et al. |
| 6,005,913 A | * | 12/1999 | Zombo et al. ................. 378/71 |
| 6,122,344 A | * | 9/2000 | Beevor ........................ 378/88 |
| 6,163,592 A | * | 12/2000 | He et al. ....................... 378/71 |
| 6,225,631 B1 | | 5/2001 | Mastrippolito et al. |
| 6,411,676 B1 | * | 6/2002 | Hooft et al. ................... 378/73 |
| 6,442,233 B1 | * | 8/2002 | Grodzins et al. ............. 378/57 |
| 6,470,067 B1 | * | 10/2002 | Harding ....................... 378/19 |
| 6,621,888 B2 | * | 9/2003 | Grodzins et al. ............. 378/57 |
| 6,744,845 B2 | * | 6/2004 | Harding et al. ............... 378/16 |
| 6,819,738 B2 | * | 11/2004 | Hoffman ..................... 378/19 |
| 6,956,928 B2 | * | 10/2005 | He et al. ....................... 378/87 |
| 6,987,836 B2 | * | 1/2006 | Tang et al. .................. 378/154 |
| 7,065,175 B2 | * | 6/2006 | Green .......................... 378/57 |
| 7,092,485 B2 | * | 8/2006 | Kravis .......................... 378/57 |
| 7,236,560 B2 | * | 6/2007 | Malamud ....................... 378/7 |
| 7,295,650 B2 | * | 11/2007 | Lange et al. .................. 378/86 |
| 2006/0104414 A1 | * | 5/2006 | Mayo ........................... 378/57 |

FOREIGN PATENT DOCUMENTS

| | | |
|---|---|---|
| DE | 195 10 168 A1 | 9/1996 |
| GB | 2 030 422 A | 4/1980 |
| GB | 1 578 881 | 11/1980 |

OTHER PUBLICATIONS

International Search Report, mailed Jul. 2, 2004, for PCT Application No. PCT/GB03/05281, 7 pages.

Datte, P. et al., "A prototype 8×8 pixel array X-ray detector for protein cystallography," *Nuclear Instruments and Methods in Physics Research A*, pp. 471-480 (1997).

Hall, C., "Letter to the Editor: Synchotron energy-dispersive X-ray diffraction tomography," *Nuclear Instruments and Methods in Physics Research B*, pp. 253-257 (1998).

Harding, G. and Schreiber, B., "Coherent X-ray scatter imaging and its applications in biomedical science and industry," *Radiation Physics and Chemistry 56*, pp. 229-245 (1999).

Harding, G. and Kosanetzky, J., "Status and outlook of coherent-x-ray scatter imaging," *J. Opt. Soc. Am. A*, vol. 4, No. 5, pp. 933-944 (May 1987).

Westmore, M.S. et al., "Angular-dependent coherent scatter measured with a diagnostic x-ray image intensifier-based imaging system," *Medical Physics*, pp. 723-733 (May 1996).

English abstract for German Patent No. DE 30 07 456, 1 page.

English abstract for German Patent No. DE 195 10 168, 1 page.

Barmcs et al., "Time and Space-Resolved Dynamic Studies on Ceramic and Cementation Materials", Journal of Synchrotron Radiation 7:167-177 part 3, May 2000.

Hall et al., "Non-Destructive Tomographic Energy-Dispersive Diffraction Imaging of the Interior of Bulk Concrete", Cement and Concrete Research 30 (3): 491-495, Mar. 2000.

Seller et al., "Two Approaches to Hybrid X-Ray Pixel Array Read Out", SPIE vol. 3774, Detectors for Crystallography and Diffraction Studies as Synchrotron Sources, 30-37, Jul. 1999.

* cited by examiner

TOMOGRAPHIC ENERGY DISPERSIVE X-RAY DIFFRACTION APPARATUS COMPRISING AN ARRAY OF DETECTORS OF ASSOCIATED COLLIMATORS

The present invention relates to a tomographic energy dispersive diffraction imaging system (TEDDI).

TEDDI is a relatively recently developed tomographic imaging system. Whereas most traditional tomographic imaging systems rely on absorptive or spectroscopic responses of a material object to invading radiation, TEDDI is unique in providing diffraction data in combination with either absorption or spectroscopic data. The user has the option of which parameter to display. For instance, pathological soft tissue specimens would be expected to show a small contrast in absorption whereas diffraction patterns will be significantly different between healthy and diseased tissue. The diffraction pattern across a friction stir weld for example will show the alloying composition and the absorption contrast will show macroscopic physical defects. As a further example, a ceramic material with a non-uniform spacial doping could be expected to show a variation in the fluorescence of the dopant across the sample but the absorption contrast map will yield little useful information.

TEDDI is thus a powerful tomographic imaging system and its development has continued over recent years, see for instance Hall et al, "Synchrotron Energy-Dispersive X-ray Diffraction Tomography", Nuclear Instruments and Methods in Physics Research Section B-Beam Interactions with Materials and Atoms, 140 (1-2): 253-257 April 1998, Barnes et al, "Time and Space-resolved Dynamic Studies on Ceramic and cementation Materials", Journal of Synchrotron Radiation 7:167-177 part 3, May 2000, and Hall et al, "Non-destructive Tomographic Energy-dispersive Diffraction Imaging of the Interior of Bulk Concrete", Cement and Concrete research 30(3):491-495 March 2000.

In a typical conventional TEDDI system a white beam from a synchrotron or laboratory X-ray source collimated to the desired spacial resolution (typically with a cross section of approximately 50 $\mu m^2$) is directed at a sample. An energy resolving detector (typically a cryogenically cooled germanium solid state detector) with associated collimator is positioned to detect X-rays diffracted at an angle appropriate to the sample under investigation and the desired structural resolution. The track of the incident X-ray beam through the sample and the angle subtended by the detector collimator aperture defines the diffracting sample volume, referred to as the diffracting "lozenge". In order to obtain a 3-D image the sample is scanned in the x, y and z directions, (typically in 50 $\mu m$ steps) and the energy dispersive diffraction pattern is recorded at each point. Since each diffracting lozenge is well defined in space a 3-D structural map can be built up over the whole sample.

A disadvantage of TEDDI systems developed to date is that the process of assembling a 3-D image (or even a 2-D image) is an extremely slow process commonly taking 14 to 16 hours even using synchrotron radiation. This makes existing TEDDI systems impractical for a laboratory based analytical tool and unsuitable for medical in-vivo applications.

It is an object of the present invention to obviate or mitigate the disadvantages of existing TEDDI systems.

According to a first aspect of the present invention there is provided a tomographic energy dispersive diffraction imaging apparatus comprising:

a support for a sample;

a radiation source for directing incident radiation at a sample mounted on the support;

detection means mounted for detecting radiation transmitted through the sample at a given angle to the direction of incidence of the radiation;

the detection means comprising:

an array of energy dispersive detectors and an array of collimators, such that each energy dispersive detector has a respective collimator associated therewith.

Using a detector/collimator array in accordance with the present invention can significantly reduce the time required to obtain an image of a sample by providing information on a plurality of sample lozenges simultaneously.

According to a second aspect of the present invention there is provided a collimator for collimating incident radiation into a collimated beam, the collimator comprising at least two spaced collimator plates or foils each provided with a collimator aperture, the collimator apertures of adjacent collimator plates or foils being aligned in the direction of the collimated beam such that incident radiation passing successively through aligned apertures of adjacent collimator plates or foils is thereby collimated.

The collimator structure according to the present invention can readily provide a densely packed array of adjacent collimators, achieving high angular resolution, ideal for use in the improved TEDDI system.

The invention also provides a method of constructing the inventive collimator wherein the collimator apertures are formed by laser drilling.

Other preferred and advantageous features of the various aspects of the present invention will be apparent from the following description.

Embodiments of the present invention will now be described, by way of example only, with reference to the accompanying drawings, in which.

Figure 1:
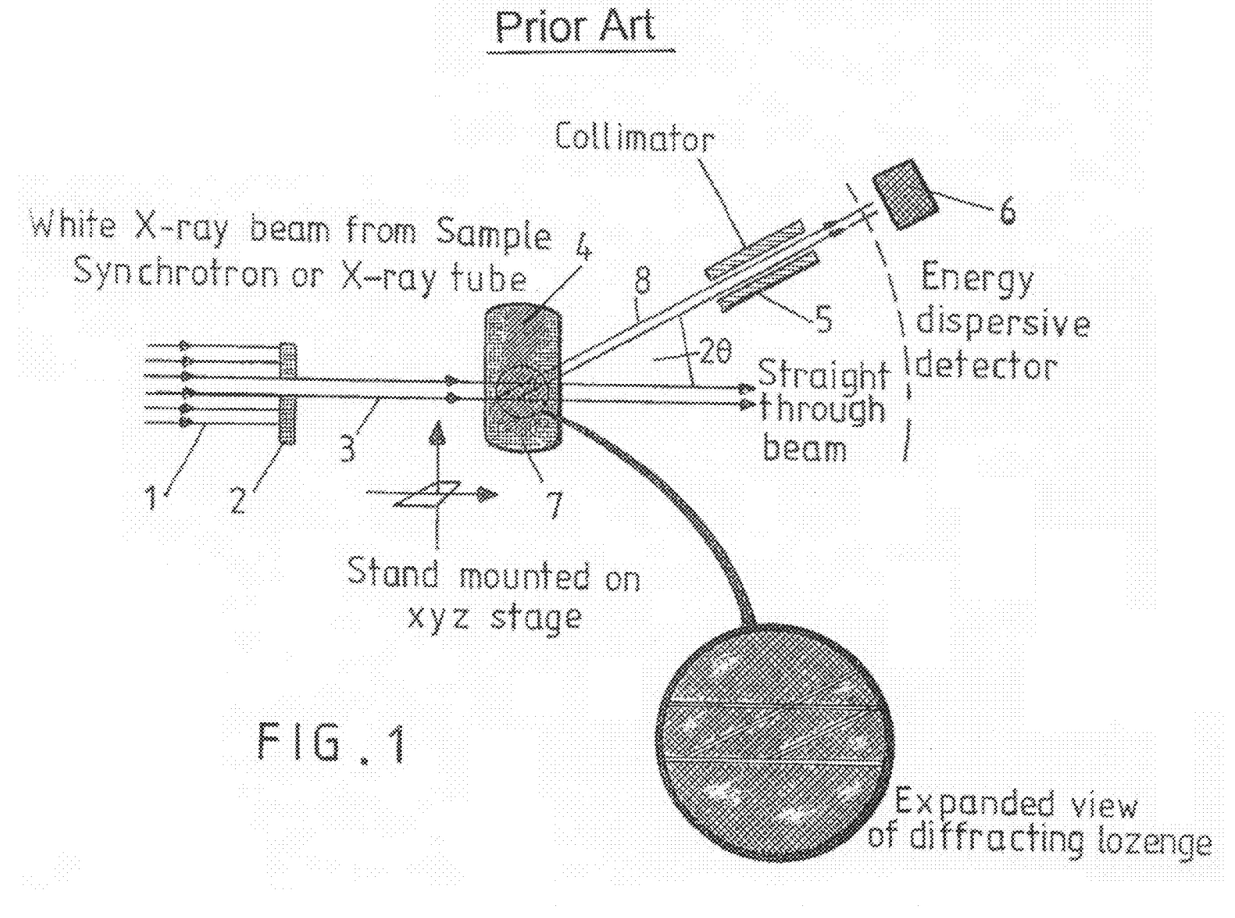
FIG. 1 is a schematic illustration of a known TEDDI system.

FIG. 1 is a schematic illustration of a known TEDDI system. A white X-ray beam 1, which may for example be produced by a synchrotron or an X-ray tube is collimated by collimator 2 to produce a beam 3 of the desired spacial resolution. In a typical system the beam will have a cross section of 50 $\mu m$. The collimated beam 3 is directed at a sample 4 which is mounted on a support (not shown) capable of scanning the sample in 3 orthogonal directions (x, y and z directions) in appropriately small steps, typically of the order of 50 $\mu m$. A deflected beam collimator 5 and energy dispersive detector 6 is positioned at an angle 2θ to the incident beam 3 (the angle is selected a appropriate to the sample under consideration and the desired structural resolution by application of Bragg's Law in a known way). The diffracting sample volume is the lozenge 7 defined by the track of the incident beam 3 and the diffracted beam 8 accepted by the collimator 5. The size of the lozenge determines the spacial resolution.

To collect energy dispersive diffraction patterns the detector 6 must have an energy resolution of the order of 2% or better. Thus, in known TEDDI systems cryogenically cooled solid-state germanium detectors are used. Conventional cryogenically cooled solid-state germanium detectors are bulky items, typically around 0.5 metres in diameter, and are very expensive costing of the order of £15,000 each.

The present inventors have recognised that a silicon pixel detector chip recently developed at the CCLRC Rutherford Appleton laboratory in Oxfordshire UK provides sufficient energy resolution in a small and relatively cheap package. The detector chip is described in the paper "Two Approaches To Hybrid X-ray Pixel Array Read Out", P. Seller, et.al., SPIE Vol. 3774, Detectors for Crystallography and Diffraction Studies as Synchrotron Sources, Jul. 1999 and consists of a 16×16 array of 300 $\mu m^2$ pixels each effectively constituting a discrete detector having an energy resolution of the order of 250 eV at 5.9 keV. This is comparable with the best quality cooled germanium detectors which have a resolution between 120 eV and 180 eV at 5.9 keV. In addition, the silicon detector count rates are of the order of 1 MHz which is adequate for tomographic studies.

Figures 2A, 2C:
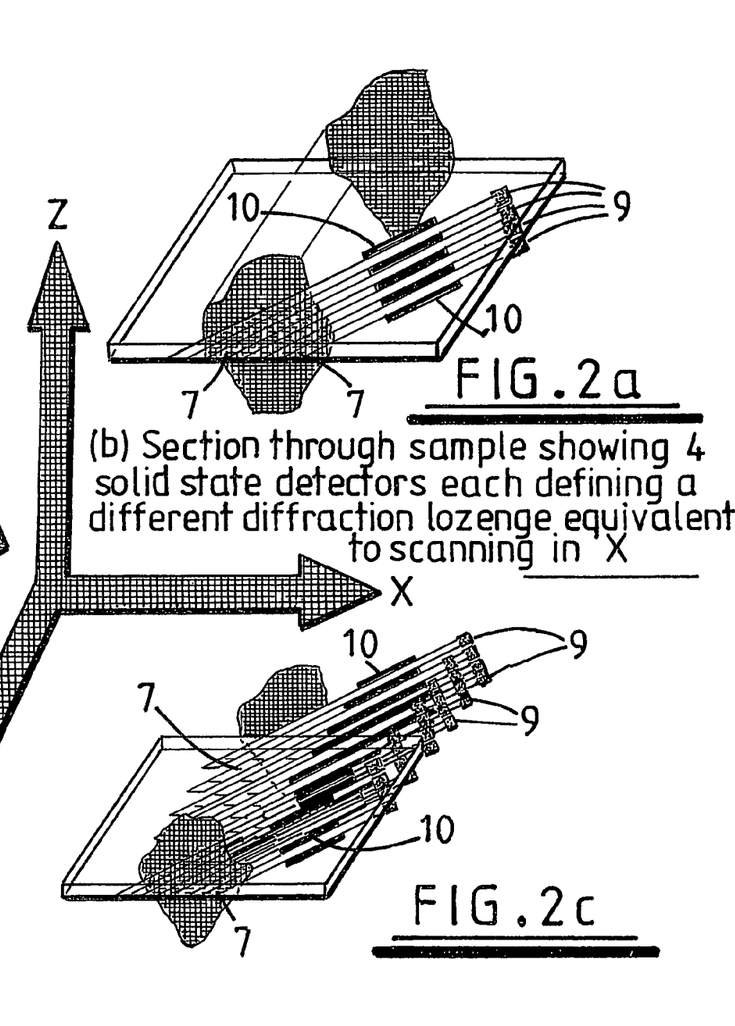
FIGS. 2a-2c schematically illustrate embodiments of part of a TEDDI system in accordance with the present invention.

Furthermore, the present inventors have recognised that by using a pixel array, detector data from a corresponding array of neighbouring detector lozenges on one plane through the sample can be obtained simultaneously. This is illustrated schematically with reference to FIGS. 2a to 2c. Referring first to FIG. 1, this illustrates the conventional single detector 6 and collimator 5 measuring data from a single diffraction lozenge 7 at a time. FIG. 2a illustrates that by arranging a plurality, in this case four, detectors 9 vertically, together with their respective collimators 10, data may be collected from four diffraction lozenges 7 simultaneously. In this case the lozenges are neighbouring along the x direction (equivalent to a corresponding x direction scan in a conventional system).

Figure 2B:
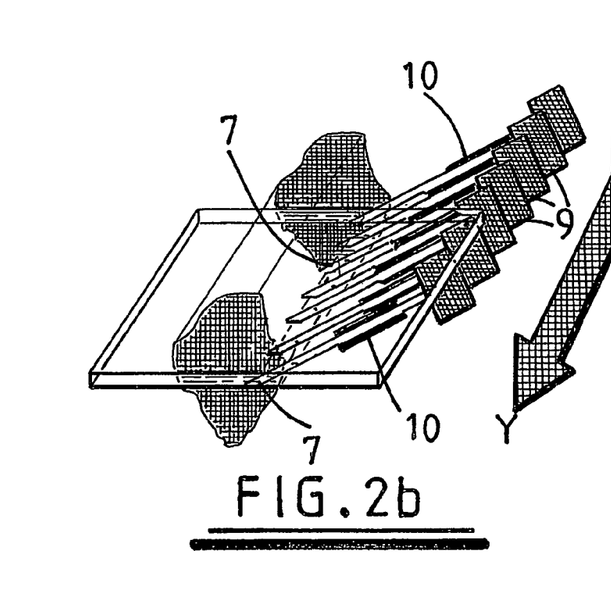

Similarly, FIG. 2b illustrates that by arranging an array of detectors 9 and collimators 10 horizontally (in the Y direction), and providing the incident beam as a vertically thin fan shape, data from neighbouring diffraction lozenges 7 in the Y direction may be collected simultaneously (equivalent to a corresponding y-direction scan in a conventional system). In the illustration there are seven detectors (or detecting pixels) and respective collimators arranged side by side providing data on seven neighbouring diffraction lozenges.

FIG. 2c illustrates the effect of providing a two dimensional array of detectors 9 and collimators 10 (again with a thin fan shaped incident beam) which provides simultaneous data from a two dimensional array of diffraction lozenges, in this case lying in the x-y plane.

It will thus readily be appreciated that by providing an array of adjacent detectors/collimators, and in particular a two dimensional array of detectors/collimators, the number of scanning movements of the sample is reduced. Moreover, if a two-dimensional array of detectors is of sufficient size to "cover" the entire sample then scanning will only be required in a single direction (the Z direction in the case of the arrangement shown in FIG. 2c) to obtain a complete set of diffraction patterns for all voxels (i.e. lozenges) of the sample. Using the silicon pixel detector chip mentioned above a single chip provides a 16×16 detector array and two dimensional detector arrays of almost any practical size can be provided by positioning a plurality of the detector chips side by side.

Whilst provision of the required planar, or fan shaped, incident beam is straightforward, collimation of the diffracted energy beams on this scale is however problematical. Tolerances on the angular collimation of the diffracted beam are small. If the collimator aperture is too large then the energy resolution of the system will be dominated by the angular aperture of the collimator rather than the intrinsic detector resolution. For example, in order to preserve an energy resolution commensurate with a sample structure spatial resolution of 1 to 1.5 Angstroms it is necessary to provide each detector with a collimator having a transmitted divergence of the order of 0.3 mrad or 0.02°. This is referred to as the angular resolution of the collimator. The required collimator resolution for any particular measurement can be determined directly from application of Bragg's Law in a known way with reference to the required energy resolution, detection angle, and spatial resolution within the sample.

Figure 3:
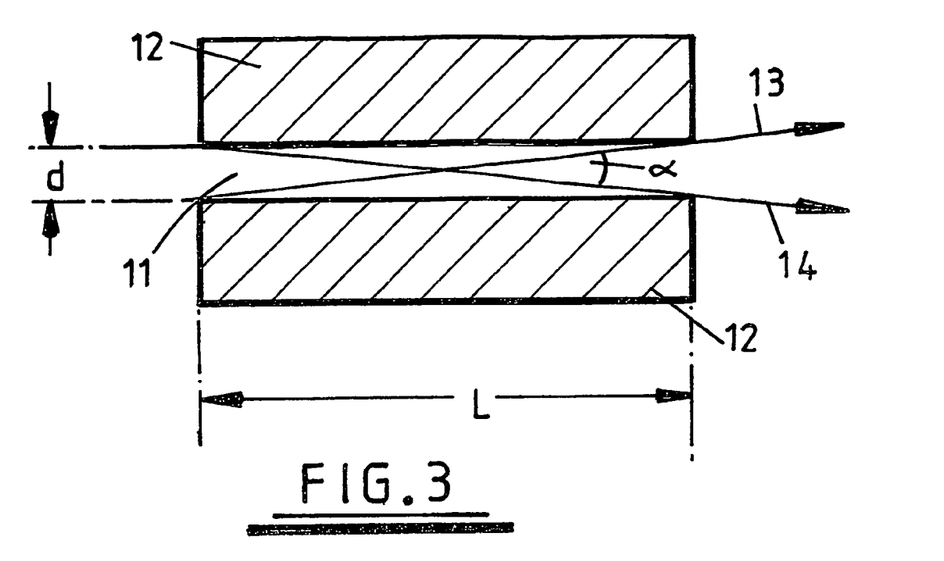
FIG. 3 is a schematic illustration of a known collimator structure.

FIG. 3 schematically illustrates the angle of resolution of a simple collimator structure comprising a bore 11 through an otherwise solid block of absorbent material 12. The scale is exaggerated for clarity. The angular resolution $\alpha$ is the angle between the most divergent rays 13/14 which may be transmitted directly through the collimator bore 11. From application of simple geometry it can be seen that the angular resolution $\alpha$ is related to the length (L) and diameter (d) of the collimator bore by the expression:

$$\tan(\alpha/2) = (d/2)/(L/2) \text{ which gives:}$$

$$\alpha = 2 \tan^{-1}(d/L) \quad (1)$$

Applying the above expression (1) it can be seen that to achieve an angular resolution of 0.02° the collimator bore must have an aspect ratio of approximately 6000:1. Thus for a typical collimated beam diameter of 50 μM the bore would need a length of approximately 300 mm to give this aspect ratio. However, even the most advanced femto laser drilling systems currently available are only able to achieve an aspect ration of 10:1 on this scale with the required degree of accuracy.

Figure 4:
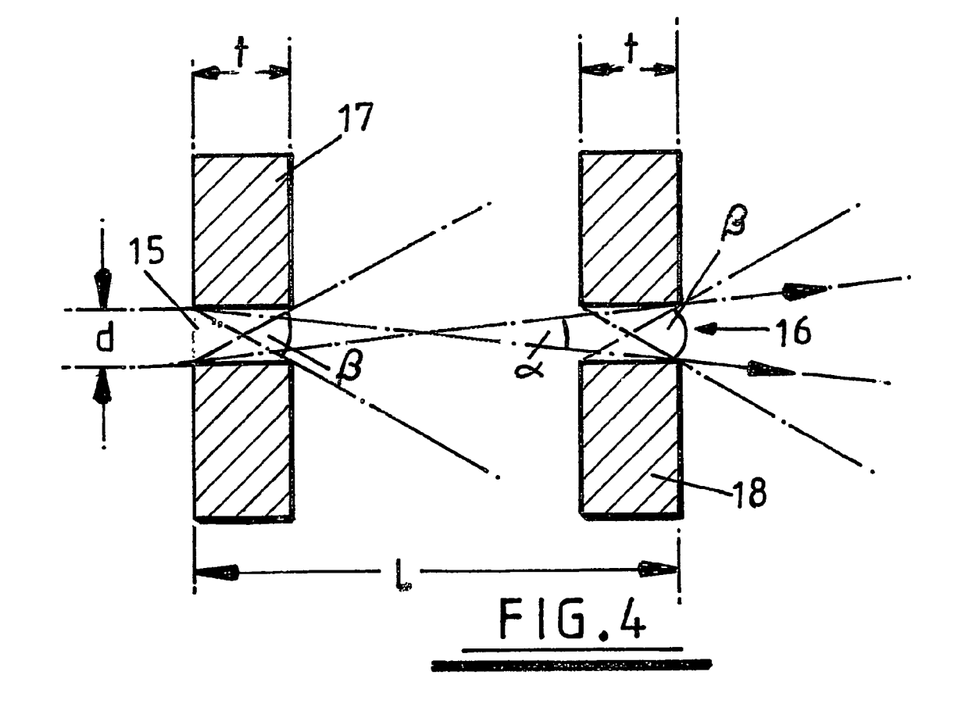
FIG. 4 is a schematic illustration of a collimator in accordance with the present invention.

Accordingly, a further aspect of the present invention is the provision of a new form of collimator which may be applied in many different applications but is particularly useful for application in the improved TEDDI system of the present invention. A simple collimator in accordance with the present invention is illustrated in FIG. 4. Again the scale is exaggerated for clarity. Rather than provision of a continuous bore through an otherwise solid block of material as illustrated in FIG. 3, an equivalent aspect ratio is achieved by providing apertures 15 and 16 of diameter d in respective thin plates or foils 17 and 18 of absorbent material which are spaced by the required distance L (measured between the front face of front collimator foil 17 and the back face of back collimator foil 18).

Each collimator foil 17, 18 has a respective angular resolution $\beta$ determined by the aperture diameter d and the thickness t of the foil. Thus, applying expression (1):

$$\beta = 2 \tan^{-1}(d/t)$$

However, the two collimator foils combine to give an overall collimator resolution of $\alpha$, which is:

$$\alpha = 2 \tan^{-1}(d/L)$$

Thus, if d and L are the same as the dimensions d and L of the simple collimator structure of FIG. 3, the collimator resolution will be the same. Accordingly, a collimator resolution of 0.02° can readily be achieved by providing 50 μm diameter apertures in respective collimator foils spaced apart so that L=300 mm.

The collimator apertures could be formed by any suitable process, but in accordance with the present invention are preferably formed by laser drilling. As mentioned above, modern laser drilling can achieve an aspect ratio of 10:1 which equates, for example, to drilling a 50 μm hole in a 0.5 mm thick foil. A practical limit of current laser drilling technology would be of the order of 10 μm holes in a 100 μm thick plate and thus to achieve smaller collimator aperture sizes other technologies, such as lithographic techniques, would be required The collimator foils could be of any suitable material and thickness. For use in a TEDDI system the foils are preferably tungsten, which is highly absorbent to high energy X-rays, and of a self supporting thickness, e.g. of the order of 0.5 mm.

Figure 5:
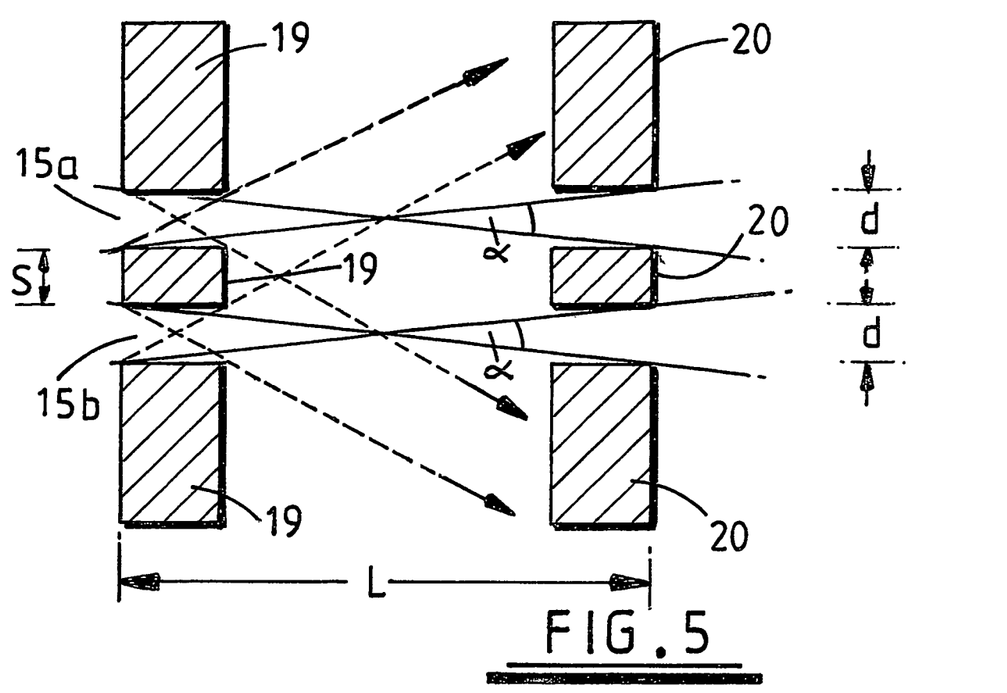
FIG. 5 is a schematic illustration of a collimator array in accordance with the present invention.

It will be appreciated that for the improved TEDDI system in accordance with the present invention an array of closely adjacent collimators is required, each collimating diffracted light for a respective one of the closely adjacent detectors (i.e. detecting pixels of the detector chip identified above). FIG. 5 schematically illustrates part of a collimator array constructed in accordance with the principals explained above in relation to FIG. 4. In FIG. 5 two adjacent collimators are shown (again not to scale for clarity) each comprising first and second collimator apertures 15a/16a and 15b/16b formed in front and back collimator foils 19 and 20. From this figure it can be seen that whilst each collimator has an angular resolution of α, there is considerable "cross-talk" between the closely adjacent collimators each of which has a much larger angular divergence β (this is indicated by the dotted ray lines), This cross-talk must be eliminated if the detected measurements are to be meaningful. This is achieved in accordance with the present invention by introducing additional collimator foils intermediate the front foil 19 and back foil 20.

Figure 6:
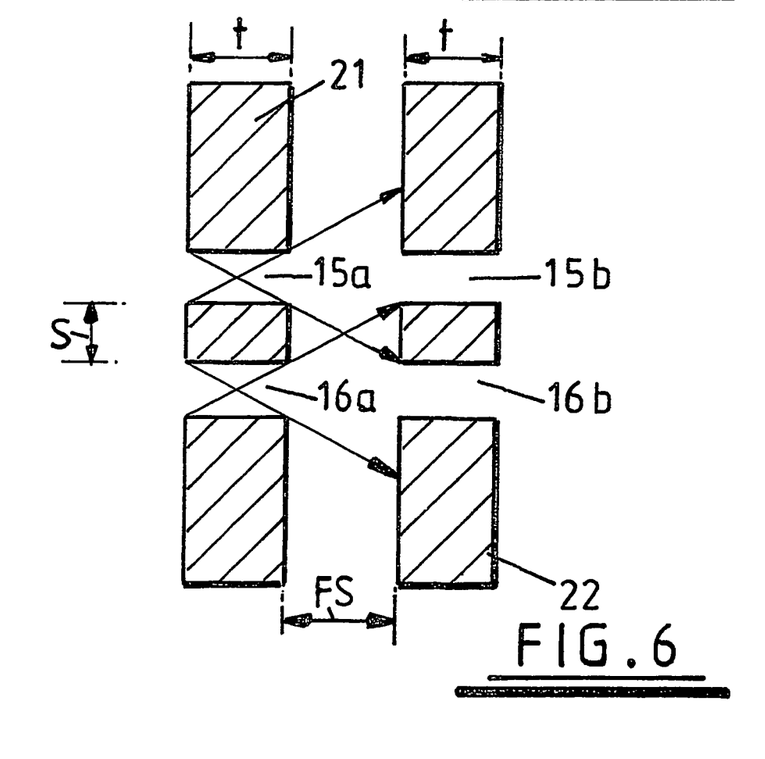
FIG. 6 is a schematic illustration of a modification of the collimator array of FIG. 5 to avoid cross-talk between adjacent collimators.

For instance FIG. 6 schematically illustrates the maximum foil separation FS between two adjacent collimator foils 21 and 22 which can be tolerated without cross-talk between adjacent collimators comprising collimator apertures 15a/16a and 15b/16b respectively. Applying simple geometry it can be seen that the maximum separation FS is related to the angular resolution β of the front foil as follows:

$\tan(\beta/2) = s/FS$ which gives:

$$FS = s/\tan(\beta/2) \quad (2)$$

or substituting $(d/2)/(t/2)$ for $\tan(\beta/2)$ gives:

$$FS = (s\,t)/d \quad (3)$$

It will also be appreciated that the overall collimator resolution of each of the collimators formed by apertures 15a/16a and 15b/16b can be determined from the expression (1) given above.

For example, assuming that each collimator foil has a thickness t of 0.5 mm, that each collimator aperture has a diameter d of 50 μm, and that the collimator aperture spacing s is 50 μm (i.e. collimator apertures centres are spaced by 100 μm) the maximum collimator foil separation avoiding cross-talk FS will be 0.5 mm.

With a foil separation FS of 0.5 mm the effective collimator length L will be 1.5 mm. Accordingly, applying expression (1) the angular resolution of each collimator in the array will be 0.38°. It may well be that this resolution is sufficient for some applications, but for the present application in which the required angular resolution would typically be of the order of 0.02° further collimator foils must be added until the overall collimator length L is sufficient to give the required aspect ratio L:d (in this case of the order of 6000:1).

Figure 7:
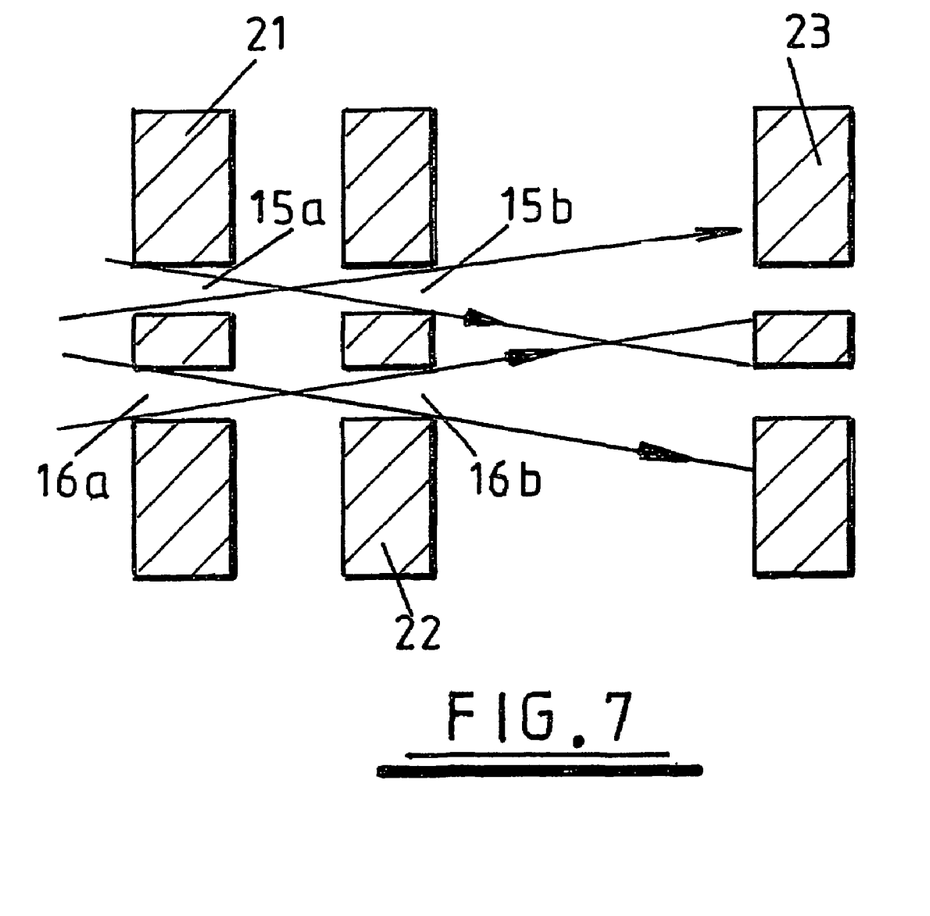
FIG. 7 is a schematic illustration of a further collimator array in accordance with the present invention.

For example adding a third collimator foil 23 to the arrangement of FIG. 6 gives the arrangement illustrated in FIG. 7 from which it will be appreciated that the maximum separation FS of the second and third collimator foils is determined by the angular diversion of the beam leaving the apertures 15b and 16b in the second collimator foil 22, i.e. the angular resolution of 0.38° provided by the combination of collimator foils 21 and 22. Thus, assuming the separation of foils 21 and 22 is the maximum of 0.5 mm, the maximum separation of foils 22 and 23 is FS=15 mm (applying expression (2) above).

Once again, the overall angular resolution of the three collimator foils is related to the distance between the front face of the front collimator foil 21 and the back face of the third collimator foil 23.

Additional collimator foils can be added as necessary until the overall collimator length is at least equal to the required distance L. The number of collimator foils required is minimised by allowing the maximum separation FS between adjacent collimator foils without cross-talk. Clearly, more than the minimum number of collimator foils may be used if desired.

As mentioned above, laser drilling is the preferred method for fabrication of the collimator structure of the present invention. A simple construction method is illustrated schematically in FIG. 8a to 8e. A first collimator foil 24 is mounted on an optical bench 25 (which may be of a conventional structure) and an aperture of required diameter d is drilled using a laser 26. Using a femtosecond laser the collimator aperture may have an aspect ratio 10:1 so that for instance a 50 μm diameter aperture could be drilled in a 0.5 mm thick foil or a 10 μm diameter aperture could be drilled in a 100 μm thick foil.

Figure 8A:
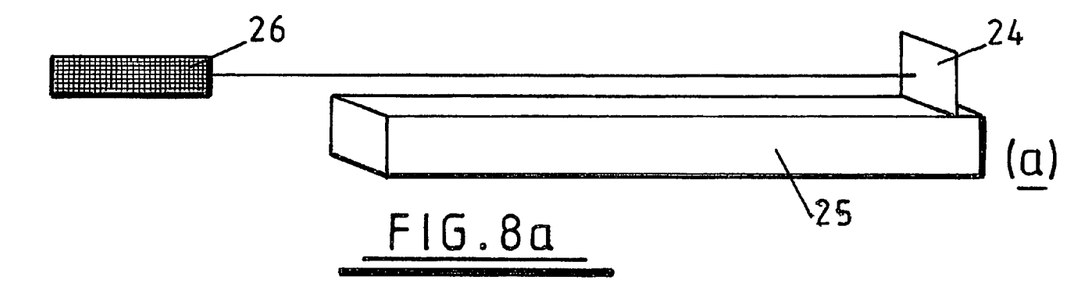
FIGS. 8a to 8e illustrate one method of constructing a collimator in accordance with the present invention.
Figure 8B:
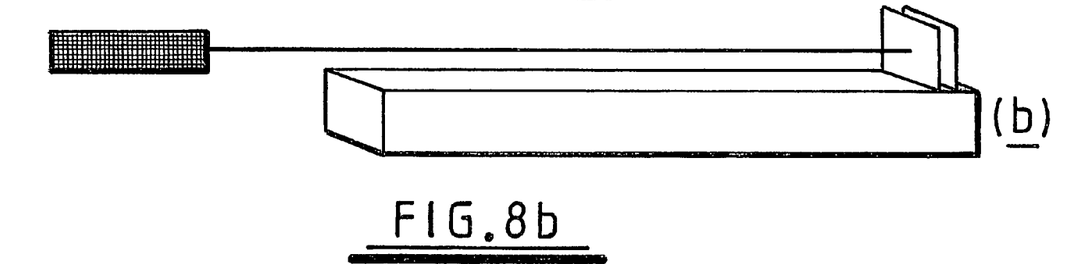

A second collimator foil is then placed on the optical bench between the laser and the first collimator foil as illustrated in FIG. 8b. A collimator aperture is then drilled in the second foil. In this way, the laser both operates to drill the required apertures and ensure that apertures of successive collimator foils are accurately aligned.

Figure 8C:
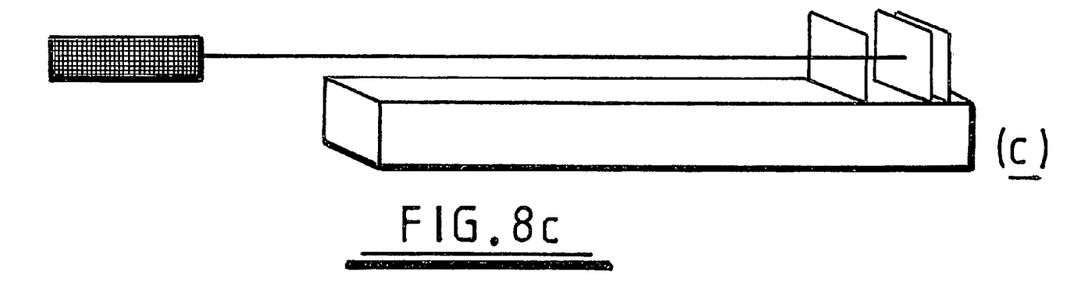
Figure 8D:
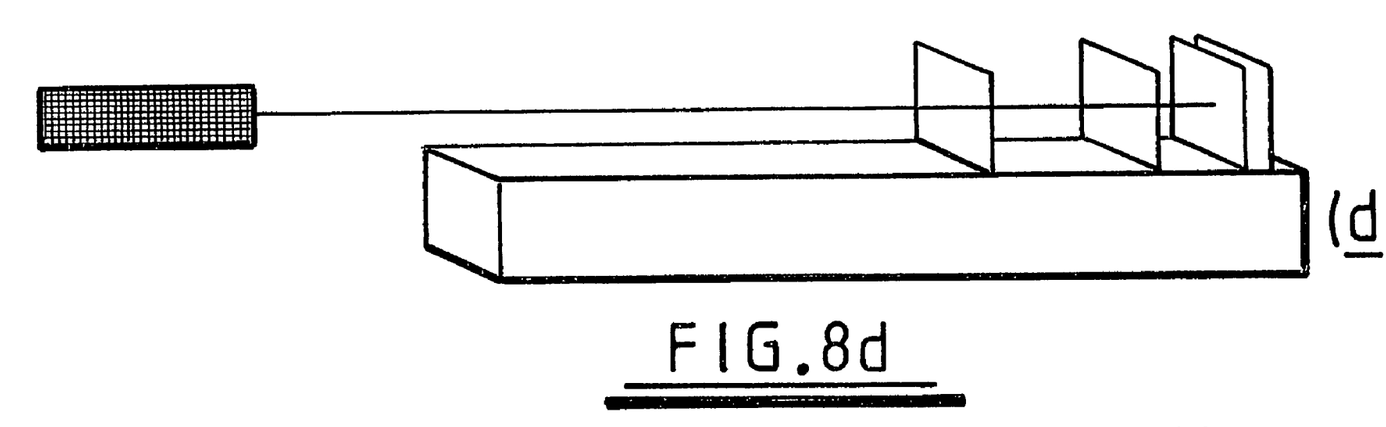
Figure 8E:
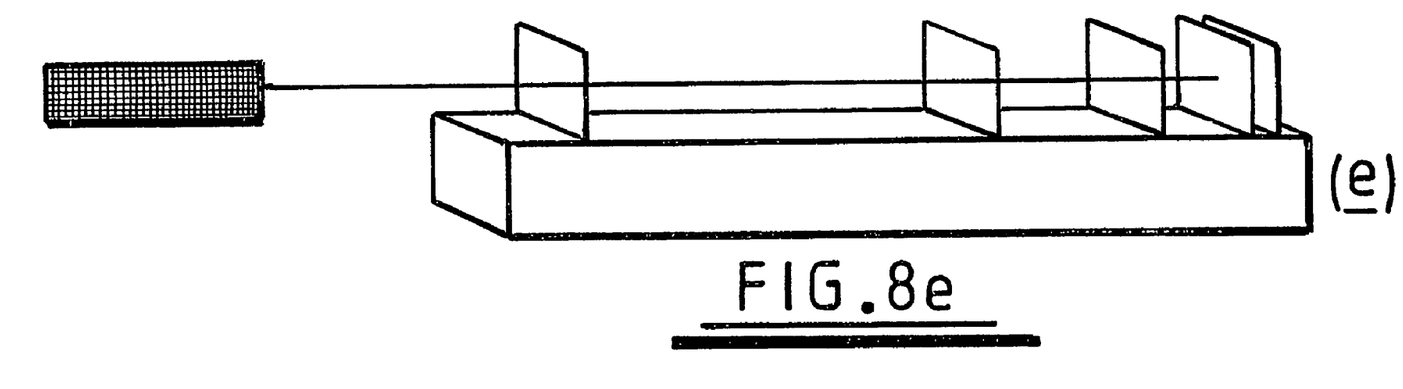

The process may then be repeated adding additional collimator foils as indicated in FIGS. 8c to 8e until the required overall collimator aspect ratio is achieved.

As a variation to the above method, each collimator foil could be removed from the optical bench after being drilled allowing the next collimator foil to be positioned at the same location as the preceding collimator foil for the drilling operation so that it is located at the laser focus. Once all collimator foils have been drilled they can then be re-mounted on the optical bench and accurately positioned with the required separation.

It will be appreciated that the laser can be used to drill an array of neighbouring collimator apertures in each of the collimator foils, in either a linear or two-dimensional array, so that the overall collimator structure comprises a similar array of individual collimators. In this case, the maximum spacing of adjacent collimator plates is calculated as mentioned above to ensure there is no cross-talk between adjacent collimators.

It will thus be appreciated that a collimator suitable for use with the detector chip technology mentioned above can readily be constructed for application in the improved TEDDI system of the present invention. It will, however, be appreciated that collimators according to the present inventions may have applications in other measurement systems.

The invention claimed is:

1. A tomographic energy dispersive diffraction apparatus comprising:
a radiation source arranged to direct a planar or fan shaped beam of radiation having a thin rectangular cross section, the beam of radiation being received at a direction of incidence at a sample; and a detector configured to detect radiation transmitted through the sample at a respective angle to the direction of incidence of the radiation, the detector comprising, a two-dimensional array of energy dispersive detectors and a two-dimensional array of collimators, the array of collimators being located between the sample and the array of energy dispersive detectors, the array of collimators being aligned with respect to the array of energy dispersive detectors, such that each collimator in the array of collimators is aligned with a corresponding one of the energy dispersive detectors, wherein each collimator of the array of collimators comprises a plurality of aligned collimator apertures formed in respective collimator plates or foils spaced apart along a direction of the transmitted radiation.

2. The apparatus according to claim 1, wherein the array of energy dispersive detectors comprises one or more semiconductor detector chips each comprising an array of individual detector pixels, each of which comprises a single detector.

3. The apparatus according to claim 1, wherein a plurality of collimator apertures are provided in each collimator plate or foil to define an array of individual collimators.

4. The apparatus according to claim 3, wherein adjacent collimator plates or foils are spaced so as to avoid cross-talk between adjacent collimators of said array of collimators.

5. The apparatus according to claim 1, wherein said angle is between 0 and 180°.

6. The apparatus according to claim 1, wherein the radiation source is provided with an incident radiation collimator for collimating incident radiation into a fan shaped beam.

* * * * *